United States Patent
Adam et al.

(10) Patent No.: US 6,890,622 B2
(45) Date of Patent: May 10, 2005

(54) COMPOSITE FLUID DISTRIBUTION AND FLUID RETENTION LAYER HAVING SELECTIVE MATERIAL DEPOSITION ZONES FOR PERSONAL CARE PRODUCTS

(75) Inventors: Gabriel Hamman Adam, Alpharetta, GA (US); Leon Eugene Chambers, Jr., Marietta, GA (US); John Herbert Conrad, Alpharetta, GA (US); Robert G. Geer, Canton, GA (US); Eric Edward Lennon, Roswell, GA (US); Sridhar Ranganathan, Suwanee, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 159 days.

(21) Appl. No.: 10/037,451

(22) Filed: Dec. 20, 2001

(65) Prior Publication Data

US 2003/0118780 A1 Jun. 26, 2003

(51) Int. Cl.$^7$ ................................................. B32B 7/02
(52) U.S. Cl. ........................ 428/171; 428/172; 428/218; 442/417; 442/327
(58) Field of Search ................................ 428/171, 172, 428/218; 442/327, 417

(56) References Cited

U.S. PATENT DOCUMENTS

| | | | |
|---|---|---|---|
| 3,670,731 A | 6/1972 | Harmon | |
| 3,766,922 A | 10/1973 | Krusko | |
| 3,802,817 A | 4/1974 | Matsuki et al. | |

(Continued)

FOREIGN PATENT DOCUMENTS

| | | |
|---|---|---|
| EP | 370 094 | 5/1990 |
| EP | 383 616 | 8/1990 |
| EP | 414 541 | 2/1991 |
| EP | 0 558 889 A1 | 9/1993 |
| EP | 958 802 | 11/1999 |
| EP | 1 022 125 | 7/2000 |
| EP | 055 403 | 11/2000 |
| EP | 1 110 528 A2 | 6/2001 |
| WO | 99/04831 | 2/1999 |
| WO | 99/51429 | 10/1999 |
| WO | 99/63922 | 12/1999 |
| WO | 99/63923 | 12/1999 |
| WO | 99/63925 | 12/1999 |
| WO | 00/27625 | 5/2000 |
| WO | 00/34567 | 6/2000 |
| WO | 00/35400 | 6/2000 |
| WO | 00/41882 | 7/2000 |
| WO | 00/47153 | 8/2000 |
| WO | WO 01/35886 A1 | 5/2001 |

*Primary Examiner*—Elizabeth M. Cole
(74) *Attorney, Agent, or Firm*—Pauley Petersen & Erickson (57) ABSTRACT

An in-line formed, non-laminated web is suitable for use as a composite fluid distribution and fluid retention layer in a disposable absorbent article. The web can be formed by selective deposition of airlaid materials including absorbents, such as pulp and superabsorbents, together with binder fibers. The web so constructed will have a plurality of intermingled lower basis weight areas and higher basis weight areas coexisting and distributed in at least a central region of the web, the alternations crossing the X axis or Y axis, or both, of the web, with the higher basis weight areas being a greater thickness in the Z-direction than the lower basis weight areas. The web so constructed will further have no discrete material boundaries between the lower basis weight stripes and the higher basis weight stripes. Further the necessity of later processing on the web to achieve a ridged structure is removed and the fibers will remain whole and undisturbed. The selective vacuum manipulation in conjunction with multiple fiber deposition heads, and appropriate timing of fiber addition therefrom, will yield a variety of useful composite webs having multiple layers thereby forming an economical single web which may be easily incorporated into an absorbent garment or article.

19 Claims, 4 Drawing Sheets

U.S. PATENT DOCUMENTS

| | | |
|---|---|---|
| 4,100,324 A | 7/1978 | Anderson et al. |
| RE29,789 E | 10/1978 | Kolbach |
| 4,223,677 A | 9/1980 | Anderson |
| 4,340,563 A | 7/1982 | Appel et al. |
| 4,375,448 A | 3/1983 | Appel et al. |
| 4,388,056 A | 6/1983 | Lee et al. |
| 4,494,278 A | 1/1985 | Kroyer et al. |
| 4,624,666 A | 11/1986 | DeRossett et al. |
| 4,640,810 A | 2/1987 | Laursen et al. |
| 4,663,220 A | 5/1987 | Wisneski et al. |
| 4,670,011 A | 6/1987 | Mesek |
| 4,685,915 A | 8/1987 | Hasse et al. |
| 4,767,825 A | 8/1988 | Pazos et al. |
| 4,781,710 A | 11/1988 | Megison et al. |
| 4,803,117 A | 2/1989 | Daponte |
| 4,820,577 A | 4/1989 | Morman et al. |
| 4,828,911 A | 5/1989 | Morman |
| 4,840,692 A | 6/1989 | Kamstrup-Larsen |
| 4,847,141 A | 7/1989 | Pazos et al. |
| 4,857,251 A | 8/1989 | Nohr et al. |
| 4,879,170 A | 11/1989 | Radwanski et al. |
| 4,929,480 A | 5/1990 | Midkiff et al. |
| 4,963,638 A | 10/1990 | Pazos et al. |
| 5,028,224 A | 7/1991 | Pieper et al. |
| 5,057,262 A | 10/1991 | Nohr et al. |
| 5,102,585 A | 4/1992 | Pieper et al. |
| 5,156,902 A | 10/1992 | Pieper et al. |
| 5,277,976 A | 1/1994 | Hogle et al. |
| 5,366,793 A | 11/1994 | Fitts, Jr. et al. |
| 5,368,926 A | 11/1994 | Thompson et al. |
| 5,382,245 A | 1/1995 | Thompson et al. |
| 5,391,161 A | 2/1995 | Hellgren et al. |
| 5,429,788 A | 7/1995 | Ribble et al. |
| 5,451,442 A | 9/1995 | Pieniak et al. |
| 5,466,409 A | 11/1995 | Partridge et al. |
| H1511 H | 12/1995 | Chappell et al. |
| 5,516,569 A | 5/1996 | Veith et al. |
| 5,527,171 A | 6/1996 | Soerensen |
| 5,558,713 A | 9/1996 | Siegfried et al. |
| 5,567,472 A | 10/1996 | Siegfried et al. |
| 5,611,879 A | 3/1997 | Morman |
| 5,618,610 A * | 4/1997 | Tomita et al. ............... 428/152 |
| 5,681,300 A | 10/1997 | Ahr et al. |
| 5,688,259 A | 11/1997 | Osborn, III et al. |
| 5,722,967 A | 3/1998 | Coles |
| 5,728,082 A | 3/1998 | Gustafsson et al. |
| 5,750,066 A | 5/1998 | Vonderhaar et al. |
| 5,788,684 A | 8/1998 | Abuto et al. |
| 5,811,178 A | 9/1998 | Adam et al. |
| 5,843,063 A | 12/1998 | Anderson et al. |
| 5,849,000 A | 12/1998 | Anjur et al. |
| 5,855,571 A | 1/1999 | Steger et al. |
| 5,885,516 A | 3/1999 | Christensen |
| 5,952,251 A | 9/1999 | Jackson et al. |
| 5,964,743 A | 10/1999 | Abuto et al. |
| 6,033,199 A | 3/2000 | Vonderhaar et al. |
| 6,127,594 A | 10/2000 | Rosseland |
| 6,133,501 A | 10/2000 | Hallock et al. |
| 6,330,735 B1 | 12/2001 | Hahn et al. |
| 6,437,214 B1 | 8/2002 | Everett et al. |
| 2001/0037101 A1 | 11/2001 | Allan et al. |
| 2002/0169430 A1 | 11/2002 | Kirk et al. |

* cited by examiner

COMPOSITE FLUID DISTRIBUTION AND FLUID RETENTION LAYER HAVING SELECTIVE MATERIAL DEPOSITION ZONES FOR PERSONAL CARE PRODUCTS

BACKGROUND OF THE INVENTION

Personal care products typically are made with a top sheet material (also referred to as a cover sheet or liner), an absorbent core and a liquid impervious back sheet. Some may also have a surge layer or other specialized layers between the top sheet and absorbent core. Absorption of fluid, comfort and avoidance of leakage are the functions desired.

An ideal absorbent product, such as the personal care products discussed herein in conjunction with the present invention, would have no leakage and deliver comfort and discretion to the user. Current personal care products may have relatively high leakage and thus offer only modest protection to the consumer. All leakage is categorized by three key causes: fluid does not absorb into the product, fluid is absorbed into the product but subsequently leaves it, or fluid never contacts the product.

The specific reasons for leakage may be expressed further in terms of definitive mechanisms. A product, for instance, may not have suitable space for absorption due to localized saturation or low contact area. The product may not have a suitable driving force for absorption because the structure does not have the right balance of permeability and capillarity. The interfiber spaces may be partially full of fluid. Fluid may contact the pad and run-off. The fluid may be too viscous or the pores or interfiber spaces are not large enough to allow fluid to pass through to the subjacent layer.

In all cases, the material systems and their concentration in a specific product design dramatically impact leakage. In the field of material systems design, leakage is a function of materials shaping and conformability as well as intake, distribution, retention and transfer.

Intake includes the initial absorption of fluid into a dry product as well as the continued uptake of that fluid into the absorbent structure. Development of superior intake systems requires an understanding of environmental conditions including the nature of the fluid and its discharge. Developing functional intake structures requires an understanding of material characteristics and their interaction with the fluid as components and systems of components including interfaces and product design. Product design includes the arrangement and geometric design of material components and their interaction with the body and fluid.

Initial intake of bodily fluids into an absorbent article is also a function of the characteristics of the liner or topsheet material and the upper absorbent layer. Intake of bodily fluid into these materials is a function of the material characteristics including the ratio of void volume to fiber surface area, fiber orientation and fiber surface wettability. These intrinsic material characteristics specifically define the more familiar material properties of permeability, capillarity and fiber wettability which can be calculated and measured by techniques well known in the art. Regardless of the characteristics of the liner, a suitable intermediate layer and absorbent core must be matched to it to permit fluid communication and transfer and thus good fluid intake.

There remains a need for a personal care product that is able to contain body exudates in such a way as to keep the wearer comfortable and protected from fluid being expressed out of the absorbent article.

As is known in the art, personal care products such as diapers or other absorbent garments are often constructed from multiple layers of materials with each layer having a specialized function. For example, two common layers are the surge layer, specialized for the rapid distribution of bodily fluids away from the point of insult to the product and the absorbent layer which is specialized to hold and retain a high volume, or load, of liquid. However, the construction of garments with specialized layers, which may be functionally very efficient, may also lead to escalating product costs due to the expense of making and placing the multiple layers together in a garment. Thus, it is further desirable that the fluid handling, or distribution, layer and the fluid absorbent, or retention layer be easily manufactured and incorporated into a personal care product in an economical fashion.

SUMMARY OF THE INVENTION

In response to the discussed difficulties and problems encountered in the prior art a new multifunctional multiple density, basis weight, or composition, web has been discovered which provides both fluid distribution and retention functions. Generally a multiple density web according to one aspect of the present invention provides a ridged structure that has higher basis weight ridges and lower basis weight valleys. Structurally the valleys are adapted to channel fluid to serve the fluid distribution function while the ridges are adapted to serve the retention function. In another aspect of the invention the high density areas may be placed in a variety of locations and patterns to aid in the overall dual functionality of the web. Personal care products using this web are also contemplated to be within the scope of this invention.

One such personal care product has a liquid impermeable backsheet, a liquid permeable topsheet, and the multifunctional multiple density web located between the topsheet and backsheet. The multifunctional multiple density web (hereinafter sometimes referred to simply as the web) according to one embodiment of the present invention is an in-line formed web having major surfaces in the X-Y plane and a depth in the Z-direction that is suitable for use as a both a fluid distribution and a fluid retention layer in a disposable absorbent article.

The web contains one or more layers of airlaid composite material which may have both thermoplastic fibers and absorbent material. The different densities of material are the result of selective deposition of the airlaid material through a process of selective vacuum application under the forming screen, also called a forming wire, on which the materials are deposited. More material is deposited in the areas of high vacuum thereby creating a higher basis weight, more lofty structure in those areas. If more than one layer is present the layers can have different density patterns or different compositions of thermoplastic fibers and absorbent material, or both, as applied in-line by various arrangements of multiple thermoplastic fiber and/or absorbent dispensers. By depositing at least two of the multiple layers in an opposing relation overlaid in the Z-axis direction of the web, a gradient can be formed in the Z-direction of the web, thereby providing fluid distribution functions when suitably arranged in that portion of the personal care product closest to the topsheet, or otherwise closest to the wearer if the topsheet is not desired or necessary. The gradient may be in the size, polymer type, construction, density, capillarity, wettability, or other known properties of the utilized materials. The low basis weight less lofty areas of the multiple density web remain in the integral differential height structure to provide fluid distribution functions without the necessity of making, handling, and constructing separate layers together into the personal care product.

Further, due to the in-line processing resulting in integral forming of high and low Z-direction areas of the web, the web need not be post-processed after forming to attain the desired differential thickness, or height, structure. Eliminating the post-processing, such as by cutting or selective application of pressure such as known in the art to achieve a ridged structure, results in the webs according to the present invention having what is termed herein as "whole fiber boundaries" between the high and low areas. That is, the fibers of the originally airlaid materials are undisturbed. By eliminating post processing of the mechanical type less dust is created and less damage to the fibers of the composite will occur. Further, without being bound by theory, it is believed that the whole fiber boundaries will result in a softer feel for the resultant web and aid in better intake and distribution of fluids including transfer between valley and ridges.

By coordinating the timing of the material deposition onto a forming wire having a controlled area vacuum, material differentials may be had along the machine direction of the web. For example, the ridges may be formed with intermittent zones of high and low concentrations of superabsorbent materials in the machine direction. Also, the in-line formed composite web may have selected Z-direction gradients of airlaid material layers and zones of different material layers intermittently placed in one of the machine direction or the cross direction. Thus the web may be customized according to the specific need for a single composite structure having fluid distribution and retention properties in a specific absorbent article application.

BRIEF DESCRIPTION OF THE DRAWINGS

A further understanding of the invention may be had with reference to the accompanying drawing figures in conjunction with the text. The figures are offered by way of aid to understanding the various embodiments of the present invention and are not to be taken as literal embodiments in exact scale or composition, and are not meant as limiting to the spirit of the present invention.

DEFINITIONS

"Disposable" includes being disposed of after a single, or limited, use and not intended to be washed and reused.

A "layer" is defined as a generally recognizable combination of similar material types or function existing in the X-Y plane.

The "upward", "upper", or "top" position is closer to the body than "downward", "lower", or "bottom" when the article is worn.

"Composite" is defined as having two or more discrete components.

As used herein and in the claims, the term "comprising" is inclusive or open-ended and does not exclude additional unrecited elements, compositional components, or method steps.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

"Spunbond fibers" refers to small diameter fibers that are formed by extruding molten thermoplastic material as filaments from a plurality of fine capillaries of a spinneret. Such a process is disclosed in, for example, U.S. Pat. No. 3,802, 817 to Matsuki et al., U.S. Pat. No. 4,340,563 to Appel et al. The fibers may also have shapes such as those described, for example, in U.S. Pat. No. 5,277,976 to Hogle et al. which describes fibers with unconventional shapes.

"Airlaying" is a well-known process by which a fibrous nonwoven layer can be formed. In the airlaying process, bundles of small fibers having typical lengths ranging from about 1 to about 19 millimeters (mm) are separated and entrained in an air supply and then deposited onto a moving forming screen, usually with the assistance of a vacuum supply. The randomly deposited fibers then are bonded to one another using, for example, hot air when thermal binders are used, or a spray adhesive, or water compaction. Airlaying is taught in, for example, U.S. Pat. No. 4,640,810 to Laursen et al. Air laying may include coform deposition which is a known variant wherein pulp or other absorbent fibers are deposited in the same air stream onto the forming screen. The screen may also be referred to herein as a forming wire. Air-laying may include multibank deposition which is known in the art to be a technique whereby multiple heads for the various fibers are located in series along the machine direction of the forming wire to serially deposit the same or different materials in layers onto the forming wire.

"Personal care product" means diapers, wipes, training pants, absorbent underpants, adult incontinence products, feminine hygiene products, wound care items like bandages, and other articles.

Words of degree, such as "about", "substantially", and the like are used herein in the sense of "at, or nearly at, when given the manufacturing and material tolerances inherent in the stated circumstances" and are used to prevent the unscrupulous infringer from unfairly taking advantage of the invention disclosure where exac t or absolute figures are stated as an aid to understanding the invention.

As used herein, the term "machine direction" or MD means the length of a fabric in the direction in which it is produced. The term "cross direction" or "cross machine direction" or CD means the width of fabric, i.e. a direction generally perpendicular to the MD.

"In-line" refers to a continuous process for forming an integral web on a single forming line, as opposed to a material constructed from multiple webs formed on multiple lines and then put together as component pieces.

"Discrete material boundaries" refer to boundaries formed between identifiable layers such as resulting from post-processing after layer formation, including, but not limited to, such processing as applying adhesives to bond separate layers, applying interlayer films or tissues, and thermal or mechanical bonding of layer boundaries creating discrete bonding lines.

DETAILED DESCRIPTION

The absorbent composites of this invention may be made using the airlaid process. The production of airlaid nonwoven composites is well defined in the literature and documented in the art. Examples include the Dan-Web process as described in U.S. Pat. No. 4,640,810 to Laursen et al. and assigned to Scan Web of North America Inc., the Kroyer process as described in U.S. Pat. No. 4,494,278 to Kroyer et al. and U.S. Pat. No. 5,527,171 to Soerensen assigned to Niro Separation a/s, the method of U.S. Pat. No. 4,375,448 to Appel et al assigned to Kimberly-Clark Corporation, or other similar methods.

In the practice of this invention an absorbent composite web having at least two integral heights, or thicknesses, of material is produced by the airlaid process. The web may include multiple layers serially deposited atop one another in the Z-direction. The number of layers may be limited in present practice by equipment constraints as most airlaying equipment currently available generally have three to seven banks of airlaying heads. However, the present invention should not be considered as so limited if it proves economical or otherwise practical to produce alternative fiber deposition equipment.

The web may have an upper layer of lower density and a lower layer of higher density wherein the upper layer is the layer closer to the body of a wearer while the personal care product is in use. The multiple density web may have various gradients in the Z, or thickness, direction including having a gradient of increasing density in the direction away from the wearer when the product is in use or otherwise. The multiple density web may also have zone, or zonal, depositions of materials, or differing concentrations of materials, as intermittently applied along at least one axis of the major X-Y, or flat, planes of the web as will be understood by those of skill in the art. The major axes of the web will be indicated in the drawings where appropriate with the thickness being indicated in the Z-direction, the X axis being indicated as the machine direction (MD) and the Y axis being indicated as the cross, or cross machine, direction (CD) for ease of explanation.

Figure 1:
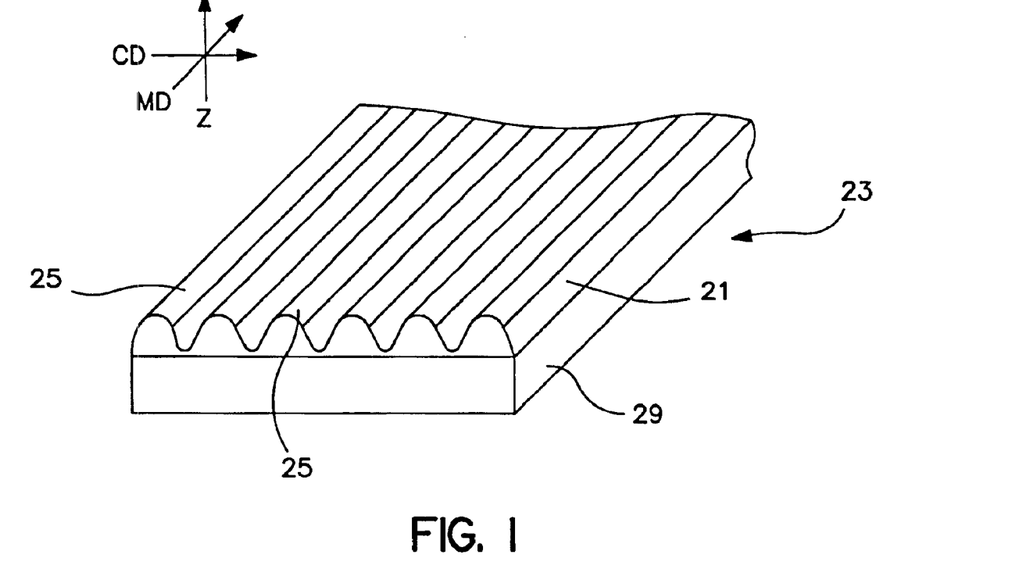
FIG. 1 is a perspective view of a first embodiment of the multiple density, basis weight, or composition web having two layers.

Referring to FIG. 1, the upper layer 21 of the exemplary embodiment of the multiple density web 23 is an airlaid, differential height layer, having ridges, collectively 25, and valleys, collectively 27, integrally formed therein by differential, or selective, vacuum deposition as further explained below. The lower layer 29 may be any of a variety of material layers but is suitably another airlaid layer of higher density than the upper layer 21 in order to further serve as the liquid retention function. The layers 21, 25 may use the same type pulp and superabsorbent, the same pulp and different superabsorbents; or different pulps and superabsorbents as the application of the web dictates. Further the material weight percents may be varied and additional materials added, or deleted, as dictated by optimum functionality for the chosen application.

Figure 2:
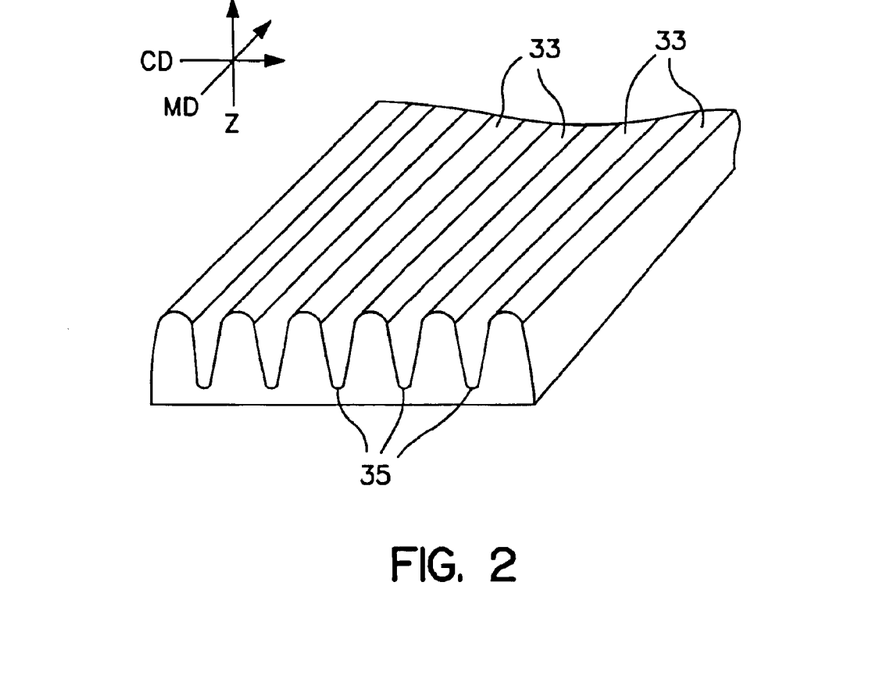
FIG. 2 is a perspective view of a second embodiment of the multiple density, basis weight, or composition web being an alternative single composition web.

Comparing FIGS. 1 and 2, it can be seen that the embodiment of FIG. 2 is a wholly integral layer 31 without the bottom layer 25 of FIG. 1. This may allow a greater differentiation of height between the ridges, collectively 33, and the valleys collectively 35, due to the unobstructed vacuum pull under the forming wire where the ridges 33 are formed. Either embodiment is contemplated by the present invention.

Binders typically used in these structures help provide mechanical integrity and stabilization. Binders include fiber, liquid or other binder means which may sometimes be thermally activated. Preferred fibers for inclusion are those having a relatively low melting point such as polyolefin fibers. Lower melting point polymers provide the ability to bond the fabric together at fiber cross-over points upon the application of heat. In addition, fibers having a lower melting polymer, like conjugate and biconstituent fibers are suitable for practice of this invention. Fibers having a lower melting polymer are generally referred to as "fuisible fibers". By "lower melting polymers" what is meant are those having a crystallinemelting temperature less than about 175 degrees C. Exemplary binder fibers include conjugate fibers of polyolefins, polyamides and polyesters. Some suitable binder fibers a re sheath core conjugate fibers available from KoSa Inc. (Charlotte, N.C.) under the designation T-255 and T-256 or a copolyester under the designation T-254, though many suitable binder fibers are known to those skilled in the art, and are available by many manufacturers such as Chisso Corporation of Osaka, Japan, and Fibervisions LLC of Wilmington, Del.

Cellulosic wood pulps used as absorbents in these airlaid structures include standard softwood fluffing grade such as CR-1654 (US Alliance Pulp Mills, Coosa, Ala.). Pulp may be modified in order to enhance the inherent characteristics of the fibers and their processability. Curl may be imparted to the fibers by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids. Some of these agents are less preferable than others due to environmental and health concerns. Pulp may also be stiffened by the use of heat or caustic treatments such as merceriΖation. Examples of these types of fibers include NHB416 which is a chemically crosslinked southern softwood pulp fibers which enhances wet modulus, available from the Weyerhaeuser Corporation of Tacoma, Wash. Other useful pulps are fully debonded pulp (NF405) and non-debonded pulp (NB416) and PH Sulfite pulp, also from Weyerhaeuser. HPZ3 from Buckeye Technologies, Inc. of Memphis, Tenn., has a chemical treatment that sets in a curl and twist, in addition to imparting added dry and wet stiffness and resilience to the fiber. Another suitable pulp is Buckeye HPF2 pulp and still another is IP SUPERSOFT® from International Paper Corporation.

Various commercially available superabsorbent materials may also be used as a component of the airlaid composites herein. The superabsorbents may be of different swell rates, morphologies, etc. and may be used singly or in combination, as will occur to those of skill in the art upon a thorough understanding of the present invention as presented herein.

It will be appreciated by those of skill in the art that various materials, as well as their amounts, and types, may be utilized according to the present invention to adapt a multiple density, basis weight, or composition web of the present invention to a variety applications while remaining within the spirit of the present invention.

One method of making the absorbent composites of this invention is by the airlaying process using multiple heads which are timed and coordinated to aid in placing the various components at certain points along the structure of the web. This may, e.g., occur in the machine direction MD where zonal separation or intermittent placement along the machine direction occurs as a function of time. Vacuum boxes will be so placed, or obstructed, as to aid in the selective deposition of the various materials on the forming wire, whether differentiated in the cross direction CD spacing, as well as having differential heights in the Z-direction. Compaction rolls, which may be heated, may be used after deposition of the layers to further control the density of the layer and to aid in bonding of the layer.

Figure 3:
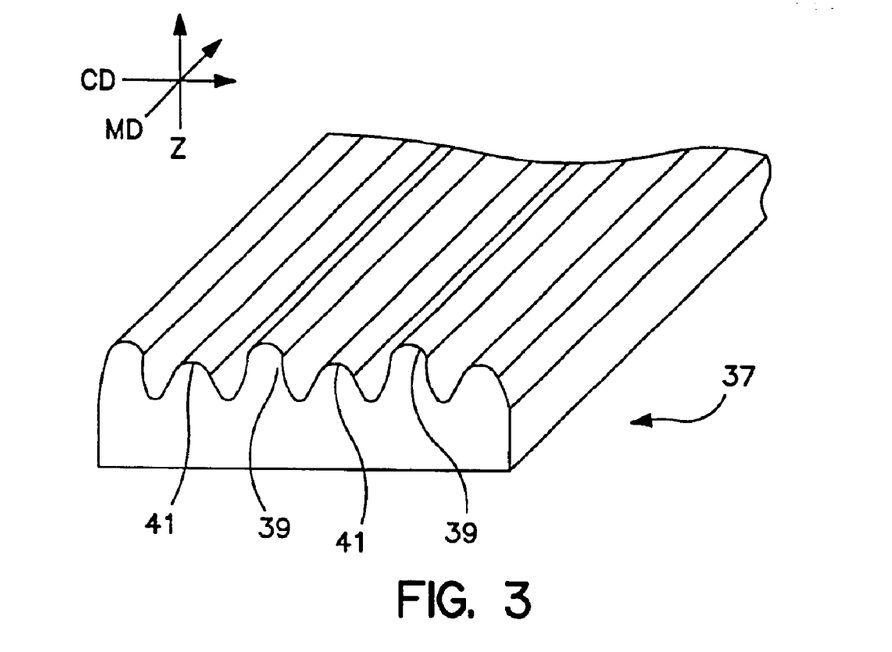
FIG. 3 is a perspective view of a third embodiment of the multiple density, basis weight, or composition web showing variation of height between the ridges.

Referencing FIG. 3, a multiple density web 37 may have ridges of a first greater height, collectively 39, and ridges of a second lesser height, collectively 41. Ridges of differential height, or multiple amplitude, may be achieved in a single layer deposition by selectively placing higher negative air pressure fluid flow under the first greater height ridges 39 than under that of the second lesser height ridges 41. Alternatively, the first greater height ridges 39 may be formed by multiple serial depositions where the negative air pressure flow has been reduced under the second lesser height ridges 41 in later depositions.

Figure 4:
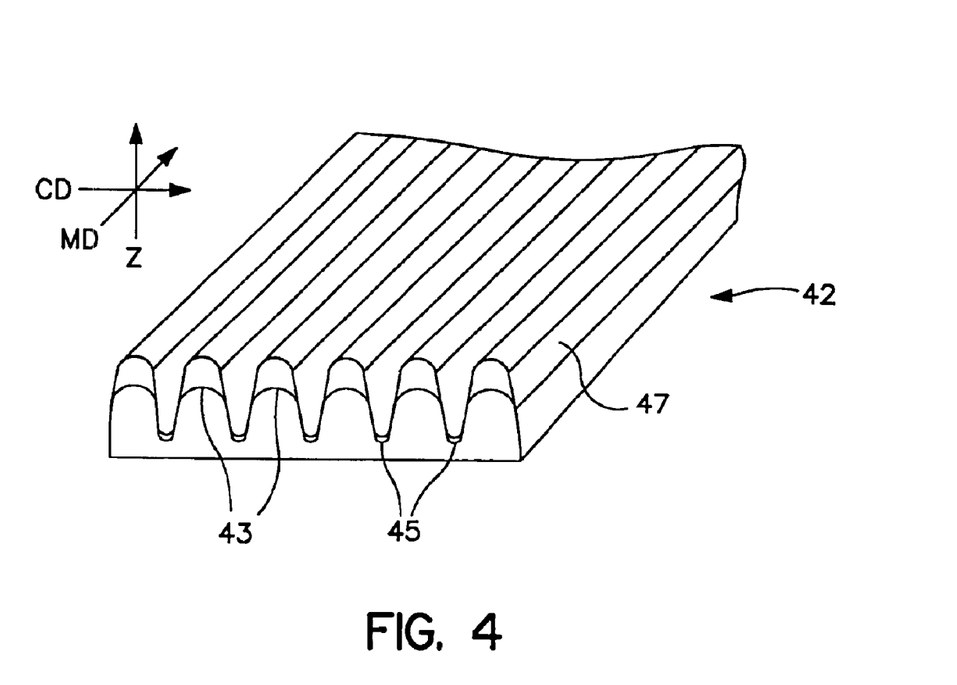
FIG. 4 is a perspective view of a fourth embodiment of the multiple density, basis weight, or composition web showing multiple layer deposition leading to Z-axis gradients while maintaining the ridged structure.

Referencing FIG. 4, a multiple density web 42 may have initial ridges, collectively 43, and valleys, collectively 45, formed in the initial layer deposition of airlaid composite materials. Thereafter, a second layer 47 is formed by serial deposition over the first deposition. The second layer 47 may be comprised of different materials, such as different denier fibers, different absorbents, and the like, or different percentages of the same material, than the initial deposition layer, thereby creating a Z-direction material gradient to aid in the fluid distribution and retention functions of the web.

Figure 5:
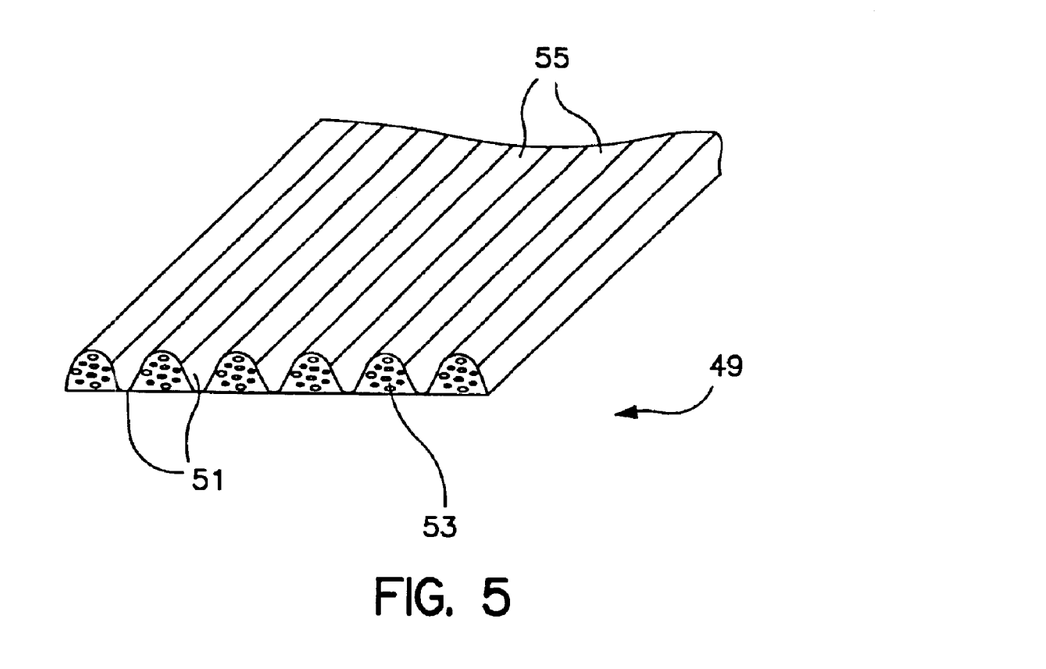
FIG. 5 is a perspective view of a fifth embodiment of the multiple density, basis weight, or composition web showing ridged areas having superabsorbent and valley areas having low or no superabsorbent.

Referencing FIG. 5, a multiple density web 49 is provided with very low density valleys, collectively 51, of almost no height. The material composition of the airlaid composite in FIG. 5 is highly loaded with superabsorbent particles 53, resulting in distinct ridges, collectively 55, carrying high concentrations of superabsorbent while the valleys 51 have little or no superabsorbent particles.

Figure 6:
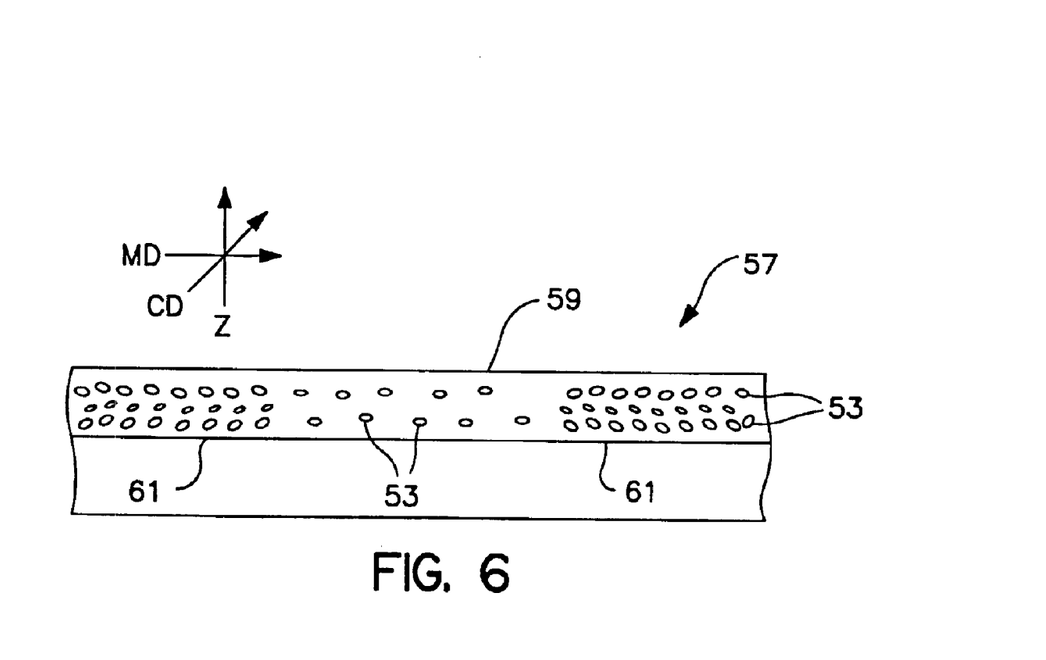
FIG. 6 is a longitudinal cross section along the machine direction of a ridge of a fifth embodiment of the multiple density, basis weight, or composition web showing zonal deposition of absorbent particle concentration in the ridge.

Referencing FIG. 6, a cross section through a ridge 57 along the machine direction MD of a multiple density web 57 shows a zone 59 of low superabsorbent particle 53 concentration between two zones 61 of high superabsorbent particle concentration. The intermittent change in the concentration of superabsorbent may be regulated through timed dispensing of differing superabsorbent concentrations as the forming web travels underneath the superabsorbent dispensing means.

Figure 7:
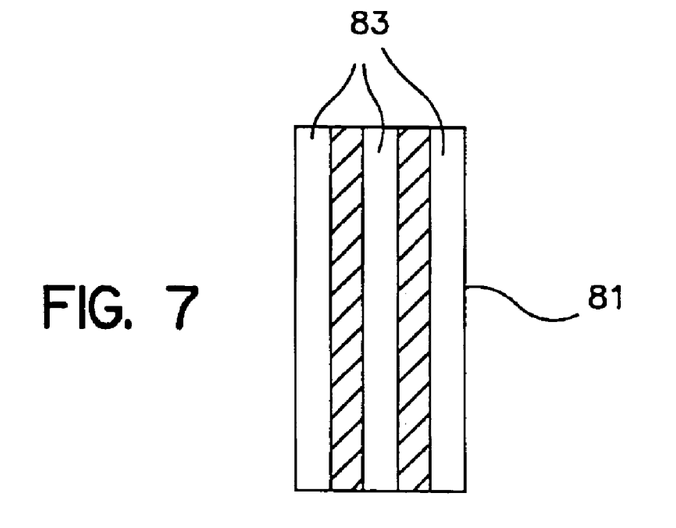
FIGS. 7 and 8 illustrate exemplary control plates that can be placed between the forming wire and the deposition vacuum to achieve different densities and patterns of material in the web.
Figure 8:
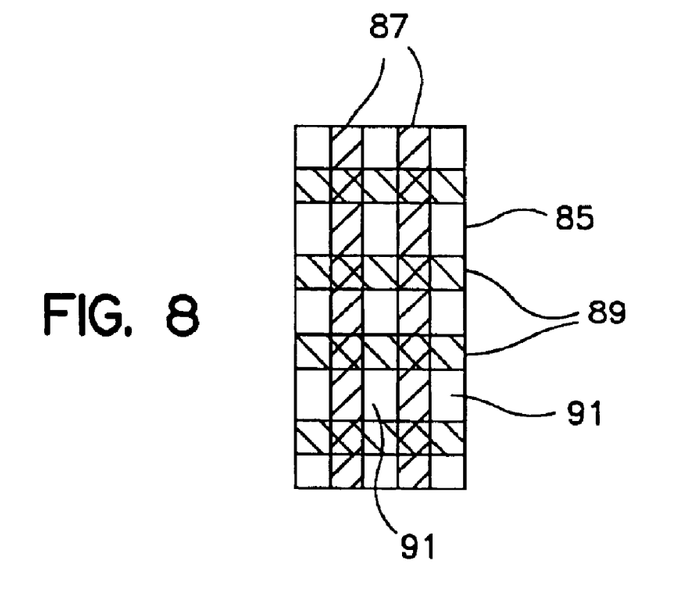

Referencing FIGS. 7 and 8, exemplary control plates are shown that can be placed between the forming wire and the deposition vacuum source to achieve different densities and patterns of material in the web. It will be understood that the open areas of the plate will lead to higher vacuum underneath the forming wire resulting in a greater deposition of airlaid fibers, and hence an area of greater height and loft in the resultant deposited layer. It will further be appreciated that the illustrated embodiments have be negative-reversed so that the illustrated open areas become closed and the closed areas open if the functionality of the web so dictates.

FIG. 7 shows a plate 81 having regularly spaced rectangular open areas 83 in a side by side stripe configuration with the open area stripes 83 extending in the machine direction of the plate 81. This plate will result in the machine direction ridge and valley webs as typified by the illustrated webs of FIGS. 1–6. FIG. 8 shows a plate 85 having a checker board pattern of closed longitudinal stripes 87 in the machine direction and closed lateral stripes 89 in the cross direction resulting in regularly spaced rows and columns of rectangular open areas 91.

The exemplary control plates are offered by way of aid to understanding the various embodiments of the present invention and are not to be taken as literal embodiments in exact scale or composition, and are not meant as limiting to the spirit of the present invention. For example the placement, number, shape, and size of the apertures therein may be varied considerably from the illustrated embodiments. Further, the plates may be utilized in series to create multiple layers of the same or different patterns overlaid on top of one another.

As will be appreciated by those skilled in the art, changes and variations to the invention are considered to be within the ability of those skilled in the art. Such changes and variations are intended by the inventors to be within the scope of the invention.

We claim:

1. An in-line formed, non-laminated, air laid web, the web having major surfaces in the X-Y plane and a depth in the Z direction, the web suitable for use as a composite fluid distribution and fluid retention layer in a disposable personal care product, comprising:
   a) a plurality of intermingled lower basis weight areas and higher basis weight areas coexisting and distributed in at least a central region of web, the lower basis weight areas and higher basis weight areas crossing the X axis or Y axis, or both, of the web;
   b) the higher basis weight areas being a greater thickness in the Z-direction than the lower basis weight areas;
   c) the web having no discrete or disturbed material boundaries between the lower basis weight areas and the higher basis weight areas, whereby whole fibers exist at the boundaries between the lower basis weight areas and the higher basis weight areas;
   d) the web further containing superabsorbent materials; and
   e) further having upper and lower areas as distinguished in the Z direction of the web, with greater hydrophilicity in the lower areas of the web; and
   f) the web being integrally formed.

2. The in-line formed, non-laminated web of claim 1, further having upper and lower areas as distinguished in the Z direction of the web, with fiber denier in the upper areas of the web larger than fiber denier in the lower areas of the web.

3. The in-line formed, non-laminated web of claim 2, further having upper and lower areas as distinguished in the Z direction of the web, with different pulps in the upper areas of the web than in the lower areas of the web.

4. The in-line formed, non-laminated web of claim 3, further having upper and lower areas as distinguished in the Z direction of the web, with different superabsorbents in the upper areas of the web than in the lower areas of the web.

5. An in-line formed, non-laminated web, the web having major surfaces in the X-Y plane and a depth in the Z direction, the web suitable for use as a composite fluid distribution and fluid retention layer in a disposable personal care product, comprising:
  a) a plurality of a lower basis weight stripes alternating with a plurality of second higher basis weight stripes in at least a central region of web, the alternations crossing at least one major axis in the plane of the web;
  b) the higher basis weight stripes being a greater thickness in the Z-direction than the lower basis weight stripes;
  c) the web having no discrete or disturbed material boundaries between the lower basis weight stripes and the higher basis weight stripes, whereby whole fibers exist at the boundaries between the lower basis weight stripes and the higher basis weight stripes; and
  d) the web further containing superabsorbent materials wherein the higher basis weight stripes have a zone of a low concentration of absorbent material and a zone of a high concentration of absorbent material alternating in the machine direction; and
  e) the web being integrally formed.

6. An in-line formed, non-laminated web, the web having major surfaces in the X-Y plane and a depth in the Z direction, the web suitable for use as a composite fluid distribution and fluid retention layer in a disposable personal care product, comprising:
  a) a plurality of a lower basis weight stripes alternating with a plurality of second higher basis weight stripes in at least a central region of web, the alternations crossing at least one major axis in the plane of the web;
  b) the higher basis weight stripes being a greater thickness in the Z-direction than the lower basis weight stripes;
  c) the web having no discrete or disturbed material boundaries between the lower basis weight stripes and the higher basis weight stripes, whereby whole fibers exist at the boundaries between the lower basis weight stripes and the higher basis weight stripes; and
  d) the web further containing superabsorbent materials wherein the higher basis weight stripes have a zone of a low concentration of absorbent material and a zone of a high concentration of absorbent material alternating in the cross direction; and
  e) the web being integrally formed.

7. An in-line formed, non-laminated, air laid web, the web having major surfaces in the X-Y plane and a depth in the Z direction, the web suitable for use as a composite fluid distribution and fluid retention layer in a disposable personal care product, comprising:
  a) a plurality of intermingled lower basis weight areas and higher basis weight areas coexisting and distributed in at least a central region of web, the lower basis weight areas and higher basis weight areas crossing the X axis or Y axis, or both, of the web;
  b) the higher basis weight areas being a greater thickness in the Z-direction than the lower basis weight areas;
  c) the web having no discrete or disturbed material boundaries between the lower basis weight areas and the higher basis weight areas, whereby whole fibers exist at the boundaries between the lower basis weight areas and the higher basis weight areas;
  d) the web further containing superabsorbent materials and further having upper and lower areas as distinguished in the Z direction of the web, with fiber denier in the upper areas of the web larger than fiber denier in the lower areas of the web.

8. An in-line formed, non-laminated, air laid web, the web having major surfaces in the X-Y plane and a depth in the Z direction, the web suitable for use as a composite fluid distribution and fluid retention layer in a disposable personal care product, comprising:
  a) a plurality of intermingled lower basis weight areas and higher basis weight areas coexisting and distributed in at least a central region of web, the lower basis weight areas and higher basis weight areas crossing the X axis or Y axis, or both, of the web;
  b) the higher basis weight areas being a greater thickness in the Z-direction than the lower basis weight areas;
  c) the web having no discrete or disturbed material boundaries between the lower basis weight areas and the higher basis weight areas, whereby whole fibers exist at the boundaries between the lower basis weight areas and the higher basis weight areas;
  d) the web further containing superabsorbent materials and further having upper and lower areas as distinguished in the Z direction of the web, with greater hydrophilicity in the lower areas of the web; and
  e) the web being integrally formed.

9. An in-line formed, non-laminated, air laid web, the web having major surfaces in the X-Y plane and a depth in the Z direction, the web suitable for use as a composite fluid distribution and fluid retention layer in a disposable personal care product, comprising:
  a) a plurality of intermingled lower basis weight areas and higher basis weight areas coexisting and distributed in at least a central region of web, the lower basis weight areas and higher basis weight areas crossing the X axis or Y axis, or both, of the web;
  b) the higher basis weight areas being a greater thickness in the Z-direction than the lower basis weight areas;
  c) the web having no discrete or disturbed material boundaries between the lower basis weight areas and the higher basis weight areas, whereby whole fibers exist at the boundaries between the lower basis weight areas and the higher basis weight areas;
  d) the web further containing superabsorbent materials and further having upper and lower areas as distinguished in the Z direction of the web, with different pulps in the upper areas of the web than in the lower areas of the web.

10. An in-line formed, non-laminated, air laid web, the web having major surfaces in the X-Y plane and a depth in the Z direction, the web suitable for use as a composite fluid distribution and fluid retention layer in a disposable personal care product, comprising:
  a) a plurality of intermingled lower basis weight areas and higher basis weight areas coexisting and distributed in at least a central region of web, the lower basis weight areas and higher basis weight areas crossing the X axis or Y axis, or both, of the web;
  b) the higher basis weight areas being a greater thickness in the Z-direction than the lower basis weight areas;
  c) the web having no discrete or disturbed material boundaries between the lower basis weight areas and the higher basis weight areas, whereby whole fibers exist at the boundaries between the lower basis weight areas and the higher basis weight areas;
  d) the web further containing superabsorbent materials and further having upper and lower areas as distinguished in the Z direction of the web, with different superabsorbents in the upper areas of the web than in the lower areas of the web.

11. The in-line formed, non-laminated web of claim 7, further having upper and lower areas as distinguished in the Z direction of the web, with greater hydrophilicity in the lower areas of the web.

12. The in-line formed, non-laminated web of claim 11, further having upper and lower areas as distinguished in the Z direction of the web, with different pulps in the upper areas of the web than in the lower areas of the web.

13. The in-line formed, non-laminated web of claim 12, further having upper and lower areas as distinguished in the Z direction of the web, with different superabsorbents in the upper areas of the web than in the lower areas of the web.

14. The in-line formed, non-laminated web of claim 9, further having upper and lower areas as distinguished in the Z direction of the web, with fiber denier in the upper areas of the web larger than fiber denier in the lower areas of the web.

15. The in-line formed, non-laminated web of claim 14, further having upper and lower areas as distinguished in the Z direction of the web, with greater hydrophilicity in the lower areas of the web.

16. The in-line formed, non-laminated web of claim 15, further having upper and lower areas as distinguished in the Z direction of the web, with different superabsorbents in the upper areas of the web than in the lower areas of the web.

17. The in-line formed, non-laminated web of claim 10, further having upper and lower areas as distinguished in the Z direction of the web, with fiber denier in the upper areas of the web larger than fiber denier in the lower areas of the web.

18. The in-line formed, non-laminated web of claim 17, further having upper and lower areas as distinguished in the Z direction of the web, with greater hydrophilicity in the lower areas of the web.

19. The in-line formed, non-laminated web of claim 18, further having upper and lower areas as distinguished in the Z direction of the web, with different pulps in the upper areas of the web than in the lower areas of the web.

* * * * *